(12) United States Patent
Breton et al.

(10) Patent No.: US 8,029,519 B2
(45) Date of Patent: Oct. 4, 2011

(54) EVERSION APPARATUS AND METHODS

(75) Inventors: Tom Breton, Palo Alto, CA (US); Steve Golden, Menlo Park, CA (US)

(73) Assignee: Medtronic, Inc., Minneapolis, MN (US)

( * ) Notice: Subject to any disclaimer, the term of this patent is extended or adjusted under 35 U.S.C. 154(b) by 872 days.

(21) Appl. No.: 11/521,152

(22) Filed: Sep. 14, 2006

(65) Prior Publication Data
US 2007/0010835 A1 Jan. 11, 2007

Related U.S. Application Data

(62) Division of application No. 10/646,254, filed on Aug. 22, 2003, now abandoned.

(51) Int. Cl.
*A61B 17/04* (2006.01)
(52) U.S. Cl. .................... 606/149; 606/113; 606/153
(58) Field of Classification Search .................. 606/108, 606/113, 139, 149, 114, 144–148, 151–156; 223/39–43; 24/15, 3.2; 600/104
See application file for complete search history.

(56) References Cited

U.S. PATENT DOCUMENTS

| | | |
|---|---|---|
| 43,098 A | 6/1864 | Cooper |
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | John |
| 1,583,271 A | 5/1926 | Biro |
| 1,625,602 A | 4/1927 | Gould et al. |
| 1,867,624 A | 7/1932 | Hoffman |
| 2,201,610 A | 5/1940 | Dawson |
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |
| 2,505,358 A | 4/1950 | Gusberg et al. |
| 2,516,710 A | 7/1950 | Mascolo |
| 2,715,486 A | 8/1955 | Marcoff-Moghadam |

(Continued)

FOREIGN PATENT DOCUMENTS
DE 0219999 3/1910
(Continued)

OTHER PUBLICATIONS

"VCS Clip Applier System," published in 1995 by Auto Suture Company, a Division of U.S. Surgical Corporation.

(Continued)

*Primary Examiner* — Kathleen Sonnett

(57) ABSTRACT

Surgical eversion apparatus for preparing a conduit for anastomosis in a human patient includes an everting member having a loop shaped portion adapted to be inserted into an end portion of a conduit harvested from a human patient and configured to fold a portion of the conduit end portion over itself when moved proximally away from the end of the conduit and along the conduit while a portion of the conduit is held fixed relative thereto. A method of everting a graft includes positioning a graft in a support device such that an end portion of the graft extends therefrom; introducing a generally looped shaped member into the end portion of the graft extending from the support device; and moving the looped shaped member over the support device to fold at least a portion of the end portion of the graft over the support device.

7 Claims, 8 Drawing Sheets

U.S. PATENT DOCUMENTS

| | | |
|---|---|---|
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,674,304 A * | 7/1972 | Swanson .................... 296/43 |
| 3,753,438 A | 8/1973 | Wood et al. |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. ............ 128/334 |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A * | 7/1980 | Sakura, Jr. .................... 606/155 |
| 4,217,902 A | 8/1980 | March |
| 4,222,594 A * | 9/1980 | Skinner ........................ 285/280 |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik .................... 128/334 |
| 4,366,819 A | 1/1983 | Kaster .......................... 128/334 |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak ...................... 128/334 |
| 4,470,533 A | 9/1984 | Schuler |
| 4,474,181 A | 10/1984 | Schenck ...................... 128/334 |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel .......................... 128/334 |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. ............... 128/334 |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck ....................... 128/334 |
| 4,595,007 A | 6/1986 | Mericle |
| 4,612,932 A | 9/1986 | Caspar et al. |
| 4,622,970 A | 11/1986 | Wozniak ...................... 128/334 |
| 4,624,255 A | 11/1986 | Schenck et al. .............. 128/334 |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak ............................ 227/19 |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,163,942 A * | 11/1992 | Rydell .......................... 606/113 |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |
| 5,234,447 A | 8/1993 | Kaster et al. .................. 606/153 |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |

| | | |
|---|---|---|
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen ............................ 606/153 |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell |
| 5,366,459 A | 11/1994 | Yoon |
| 5,366,462 A | 11/1994 | Kaster et al. ................... 606/153 |
| 5,366,479 A | 11/1994 | McGarry et al. |
| 5,374,268 A | 12/1994 | Sander |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield |
| 5,403,333 A | 4/1995 | Kaster et al. ................... 606/151 |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmiedling et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck ....................... 606/153 |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,519,937 A * | 5/1996 | Soriano et al. ................... 29/842 |
| 5,522,884 A | 6/1996 | Wright |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Bennett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim ............................ 606/108 |
| 5,683,417 A | 11/1997 | Cooper |
| 5,690,662 A | 11/1997 | Chiu et al. |
| 5,695,504 A | 12/1997 | Gifford, III et al. .......... 606/153 |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon ............................ 604/164 |
| 5,707,380 A | 1/1998 | Hinchliffe ..................... 606/153 |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov ........................ 606/139 |
| 5,725,539 A | 3/1998 | Matern |
| 5,725,542 A | 3/1998 | Yoon |
| 5,728,135 A | 3/1998 | Bregen et al. |
| 5,732,872 A | 3/1998 | Bolduc et al. .............. 227/176.1 |
| 5,735,290 A | 4/1998 | Sterman et al. |
| 5,746,753 A | 5/1998 | Sullivan et al. |
| 5,755,778 A | 5/1998 | Kleshinski |
| 5,762,646 A * | 6/1998 | Cotter .......................... 604/410 |
| 5,766,189 A | 6/1998 | Matsumo |
| 5,769,870 A | 6/1998 | Salahich et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. .......... 606/153 |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe ..................... 606/153 |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. ................. 606/153 |
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |
| 5,893,369 A | 4/1999 | LeMole |
| 5,893,865 A | 4/1999 | Swindle et al. |

| | | |
|---|---|---|
| 5,893,886 A | 4/1999 | Zegdi et al. |
| 5,895,394 A | 4/1999 | Kienzle et al. |
| 5,904,697 A | 5/1999 | Gifford, III et al. |
| 5,908,428 A | 6/1999 | Scirica et al. |
| 5,911,352 A | 6/1999 | Racenet et al. |
| 5,919,207 A | 7/1999 | Taheri |
| 5,931,842 A | 8/1999 | Goldsteen et al. |
| 5,941,434 A | 8/1999 | Green |
| 5,941,442 A | 8/1999 | Geiste et al. |
| 5,941,888 A | 8/1999 | Wallace et al. |
| 5,941,908 A | 8/1999 | Goldsteen et al. |
| 5,944,730 A | 8/1999 | Nobles et al. |
| 5,951,576 A | 9/1999 | Wakabayashi ............... 606/151 |
| 5,951,600 A | 9/1999 | Lemelson |
| 5,954,735 A | 9/1999 | Rygaard ...................... 606/153 |
| 5,957,363 A | 9/1999 | Heck |
| 5,957,938 A | 9/1999 | Zhu et al. ...................... 606/149 |
| 5,957,940 A | 9/1999 | Tanner et al. |
| 5,961,481 A | 10/1999 | Sterman et al. |
| 5,961,539 A | 10/1999 | Northrup, III et al. |
| 5,964,772 A | 10/1999 | Bolduc et al. |
| 5,964,782 A | 10/1999 | Lafontaine et al. |
| 5,972,024 A | 10/1999 | Northrup, III et al. |
| 5,976,159 A | 11/1999 | Bolduc et al. ................ 606/142 |
| 5,976,161 A | 11/1999 | Kirsch et al. ................. 606/149 |
| 5,976,164 A | 11/1999 | Bencini et al. |
| 5,976,178 A | 11/1999 | Goldsteen et al. |
| 5,984,917 A | 11/1999 | Fleischman et al. |
| 5,984,959 A | 11/1999 | Robertson et al. |
| 5,989,242 A | 11/1999 | Saadat et al. |
| 5,989,268 A | 11/1999 | Pugsley, Jr. et al. |
| 5,989,276 A | 11/1999 | Houser et al. |
| 5,989,278 A | 11/1999 | Mueller |
| 5,993,468 A | 11/1999 | Rygaard ...................... 606/151 |
| 5,997,556 A | 12/1999 | Tanner |
| 6,001,110 A | 12/1999 | Adams |
| 6,007,544 A | 12/1999 | Kim |
| 6,010,531 A | 1/2000 | Donlon et al. |
| 6,013,084 A | 1/2000 | Ken et al. |
| 6,022,367 A | 2/2000 | Sherts |
| 6,024,748 A | 2/2000 | Manzo et al. ................. 606/153 |
| 6,032,849 A | 3/2000 | Mastri et al. |
| 6,033,419 A | 3/2000 | Hamblin, Jr. et al. |
| 6,036,699 A | 3/2000 | Andreas et al. |
| 6,036,703 A | 3/2000 | Evans et al. |
| 6,036,710 A | 3/2000 | McGarry et al. |
| 6,042,607 A | 3/2000 | Williamson et al. |
| 6,056,751 A | 5/2000 | Fenton |
| 6,063,070 A | 5/2000 | Eder |
| 6,066,148 A | 5/2000 | Rygaard ...................... 606/153 |
| 6,074,401 A | 6/2000 | Gardiner et al. |
| 6,074,418 A | 6/2000 | Buchanan et al. |
| 6,077,291 A | 6/2000 | Das |
| 6,080,114 A | 6/2000 | Russin |
| 6,083,237 A | 7/2000 | Huitema et al. |
| 6,106,538 A | 8/2000 | Shiber |
| 6,110,188 A | 8/2000 | Narciso .......................... 606/153 |
| 6,113,611 A | 9/2000 | Allen et al. |
| 6,113,612 A | 9/2000 | Swanson et al. |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,149,658 A | 11/2000 | Gardiner et al. |
| 6,152,935 A | 11/2000 | Kammerer et al. |
| 6,152,937 A | 11/2000 | Peterson et al. |
| 6,159,165 A | 12/2000 | Ferrera et al. |
| 6,159,225 A | 12/2000 | Makower |
| 6,165,183 A | 12/2000 | Kuehn et al. |
| 6,165,185 A | 12/2000 | Shennib et al. |
| 6,171,320 B1 | 1/2001 | Monassevitch |
| 6,171,321 B1 | 1/2001 | Gifford, III et al. |
| 6,176,413 B1 | 1/2001 | Heck et al. |
| 6,176,864 B1 | 1/2001 | Chapman ...................... 606/153 |
| 6,179,840 B1 | 1/2001 | Bowman |
| 6,179,848 B1 | 1/2001 | Solem .......................... 606/153 |
| 6,179,849 B1 | 1/2001 | Yencho et al. |
| 6,183,512 B1 | 2/2001 | Howanec et al. |
| 6,190,373 B1 | 2/2001 | Palermo et al. |
| 6,193,733 B1 | 2/2001 | Adams |
| 6,193,734 B1 | 2/2001 | Bolduc et al. ................. 606/153 |
| 6,197,037 B1 | 3/2001 | Hair |
| 6,217,611 B1 | 4/2001 | Klostermeyer |
| 6,221,083 B1 | 4/2001 | Mayer |
| 6,241,738 B1 | 6/2001 | Dereume |
| 6,241,741 B1 | 6/2001 | Duhaylongsod et al. ...... 606/153 |
| 6,248,117 B1 | 6/2001 | Blatter |
| 6,250,308 B1 | 6/2001 | Cox |
| 6,254,615 B1 | 7/2001 | Bolduc et al. |
| 6,269,819 B1 | 8/2001 | Oz et al. |
| 6,280,460 B1 | 8/2001 | Bolduc et al. |
| 6,283,979 B1 | 9/2001 | Mers Kelly et al. |
| 6,283,993 B1 | 9/2001 | Cosgrove et al. |
| 6,296,622 B1 | 10/2001 | Kurz et al. |
| 6,296,656 B1 | 10/2001 | Bolduc et al. |
| 6,306,141 B1 | 10/2001 | Jervis |
| 6,332,893 B1 | 12/2001 | Mortier et al. |
| 6,346,074 B1 | 2/2002 | Roth |
| 6,346,112 B2 | 2/2002 | Adams |
| 6,350,269 B1 | 2/2002 | Shipp et al. |
| 6,352,543 B1 | 3/2002 | Cole ............................. 606/153 |
| 6,358,258 B1 | 3/2002 | Arcia et al. |
| 6,361,559 B1 | 3/2002 | Houser et al. ................. 623/1.36 |
| 6,368,348 B1 | 4/2002 | Gabbay |
| 6,371,964 B1 | 4/2002 | Vargas et al. ................. 606/153 |
| 6,387,105 B1 | 5/2002 | Gifford, III et al. |
| 6,391,038 B2 | 5/2002 | Vargas et al. ................. 606/153 |
| 6,402,764 B1 | 6/2002 | Hendricksen ................. 606/149 |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. ................. 606/153 |
| 6,419,695 B1 | 7/2002 | Gabbay |
| 6,425,900 B1 | 7/2002 | Knodel et al. |
| 6,428,550 B1 | 8/2002 | Vargas et al. ................. 606/153 |
| 6,428,555 B1 | 8/2002 | Koster, Jr. |
| 6,451,048 B1 | 9/2002 | Berg et al. |
| 6,461,320 B1 | 10/2002 | Yencho et al. .................... 604/8 |
| 6,475,222 B1 | 11/2002 | Berg et al. ..................... 606/108 |
| 6,478,804 B2 | 11/2002 | Vargas et al. ................. 606/153 |
| 6,485,496 B1 | 11/2002 | Suyker et al. ................. 606/153 |
| 6,491,707 B2 | 12/2002 | Makower et al. |
| 6,497,671 B2 | 12/2002 | Ferrera et al. |
| 6,497,710 B2 | 12/2002 | Yencho et al. ................. 606/153 |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,288 B2 | 3/2003 | Vargas et al. ................. 606/153 |
| 6,547,799 B2 | 4/2003 | Hess et al. ..................... 606/149 |
| 6,551,332 B1 | 4/2003 | Nguyen et al. |
| 6,562,053 B2 | 5/2003 | Schulze et al. ................ 606/149 |
| 6,575,985 B2 | 6/2003 | Knight et al. .................. 606/149 |
| 6,589,255 B2 | 7/2003 | Schulze et al. ................ 606/149 |
| 6,607,541 B1 | 8/2003 | Gardiner et al. |
| 6,607,542 B1 | 8/2003 | Wild |
| 6,613,059 B2 | 9/2003 | Schaller et al. |
| 6,629,988 B2 | 10/2003 | Weadock |
| 6,635,214 B2 | 10/2003 | Rapacki et al. ................ 264/250 |
| 6,641,593 B1 | 11/2003 | Schaller et al. |
| 6,648,900 B2 | 11/2003 | Fleischman et al. ........... 606/153 |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. ................. 606/153 |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,709,442 B2 | 3/2004 | Miller et al. |
| 6,712,829 B2 | 3/2004 | Schulze ......................... 606/149 |
| 6,719,768 B1 | 4/2004 | Cole et al. ..................... 606/153 |
| 6,743,243 B1 | 6/2004 | Roy et al. |
| 6,749,622 B2 | 6/2004 | McGuckin et al. |

| | | | | | | |
|---|---|---|---|---|---|---|
| 6,776,782 B2 | 8/2004 | Schulze ............... 606/149 | DE | 19732234 | 1/1999 | |
| 6,776,784 B2 | 8/2004 | Ginn | EP | 0072232 | 2/1983 | |
| 6,776,785 B1 | 8/2004 | Yencho et al. | EP | 0122046 | 3/1983 | |
| 6,802,847 B1 | 10/2004 | Carson et al. ........... 606/153 | EP | 0129441 | 12/1984 | |
| 6,821,286 B1 | 11/2004 | Carranza et al. ........ 606/153 | EP | 0130037 | 1/1985 | |
| 6,869,444 B2 | 3/2005 | Gabbay | EP | 0140557 | 5/1985 | |
| 6,913,607 B2 | 7/2005 | Ainsworth et al. | EP | 0121362 | 9/1987 | |
| 6,918,917 B1 | 7/2005 | Nguyen et al. | EP | 0409569 | 1/1991 | |
| 6,921,407 B2 | 7/2005 | Nguyen et al. | EP | 0432692 | 6/1991 | |
| 6,926,730 B1 | 8/2005 | Nguyen et al. | EP | 0478949 | 8/1991 | |
| 6,945,980 B2 | 9/2005 | Nguyen et al. | EP | 0494636 | 7/1992 | |
| 6,955,679 B1 | 10/2005 | Hendricksen et al. ..... 606/149 | EP | 0537955 | 4/1993 | |
| 6,960,221 B2 | 11/2005 | Ho et al. | EP | 0559429 | 9/1993 | |
| 6,979,337 B2 * | 12/2005 | Kato ..................... 606/149 | EP | 0598529 | 5/1994 | |
| 6,979,338 B1 | 12/2005 | Loshakove et al. ....... 606/153 | EP | 0326426 | 12/1994 | |
| 7,022,131 B1 | 4/2006 | Derowe et al. ........... 623/1.11 | EP | 0419597 | 12/1994 | |
| 7,056,330 B2 | 6/2006 | Gayton | EP | 0632999 | 1/1995 | |
| 7,063,711 B1 | 6/2006 | Loshakove et al. ....... 606/153 | EP | 0641546 | 3/1995 | |
| 7,070,618 B2 | 7/2006 | Streeter | EP | 0656191 | 6/1995 | |
| 7,182,769 B2 | 2/2007 | Ainsworth et al. | EP | 0687446 | 12/1995 | |
| 7,220,268 B2 | 5/2007 | Blatter | EP | 0705568 | 4/1996 | |
| 2001/0018592 A1 | 8/2001 | Schaller et al. | EP | 0711532 | 5/1996 | |
| 2001/0018593 A1 | 8/2001 | Nguyen et al. | EP | 0705569 | 10/1996 | |
| 2001/0018611 A1 | 8/2001 | Solem et al. | EP | 0734697 | 10/1996 | |
| 2001/0021856 A1 | 9/2001 | Bolduc et al. | EP | 0778005 | 6/1997 | |
| 2001/0047181 A1 | 11/2001 | Ho et al. | EP | 0815795 | 1/1998 | |
| 2002/0010490 A1 | 1/2002 | Schaller et al. | GB | 2223410 | 4/1990 | |
| 2002/0042623 A1 | 4/2002 | Blatter et al. | JP | 07308322 | 11/1995 | |
| 2002/0065527 A1 * | 5/2002 | Kato ..................... 606/149 | JP | 08336544 | 12/1996 | |
| 2002/0082614 A1 | 6/2002 | Logan et al. | JP | 10337291 | 12/1998 | |
| 2002/0099395 A1 | 7/2002 | Acampora et al. | RU | 2110222 | 5/1998 | |
| 2002/0151916 A1 | 10/2002 | Muramatsu et al. | SU | 577022 | 10/1977 | |
| 2002/0165561 A1 | 11/2002 | Ainsworth et al. | SU | 1186199 | 10/1985 | |
| 2002/0173803 A1 | 11/2002 | Yang et al. | SU | 1456109 | 2/1989 | |
| 2003/0074012 A1 | 4/2003 | Nguyen et al. | SU | 1560133 | 4/1990 | |
| 2003/0078603 A1 | 4/2003 | Schaller et al. | WO | 90/06725 | 6/1990 | |
| 2003/0083742 A1 | 5/2003 | Spence et al. | WO | 90/09149 | 8/1990 | |
| 2003/0093118 A1 | 5/2003 | Ho et al. | WO | 90/14795 | 12/1990 | |
| 2003/0125755 A1 | 7/2003 | Schaller et al. | WO | 91/07916 | 6/1991 | |
| 2003/0191481 A1 | 10/2003 | Nguyen et al. | WO | 91/08708 | 6/1991 | |
| 2003/0195531 A1 | 10/2003 | Nguyen et al. | WO | 91/17712 | 11/1991 | |
| 2003/0199974 A1 | 10/2003 | Lee et al. | WO | 92/05828 | 4/1992 | |
| 2004/0050393 A1 | 3/2004 | Golden et al. | WO | 92/12676 | 8/1992 | |
| 2004/0068276 A1 | 4/2004 | Golden et al. | WO | 92/22041 | 12/1992 | |
| 2004/0102797 A1 | 5/2004 | Golden et al. | WO | 93/01750 | 2/1993 | |
| 2004/0111099 A1 | 6/2004 | Nguyen et al. | WO | 94/15535 | 7/1994 | |
| 2004/0138685 A1 | 7/2004 | Clague et al. | WO | 94/15537 | 7/1994 | |
| 2004/0176663 A1 | 9/2004 | Edoga | WO | 96/00035 | 1/1996 | |
| 2004/0193259 A1 | 9/2004 | Gabbay | WO | 96/06565 | 3/1996 | |
| 2005/0004582 A1 | 1/2005 | Edoga | WO | 96/38090 | 12/1996 | |
| 2005/0021054 A1 | 1/2005 | Ainsworth et al. | WO | 97/12555 | 4/1997 | |
| 2005/0043749 A1 | 2/2005 | Breton et al. | WO | 97/16122 | 5/1997 | |
| 2005/0065601 A1 | 3/2005 | Lee et al. | WO | 97/27898 | 8/1997 | |
| 2005/0070924 A1 | 3/2005 | Schaller et al. | WO | 97/28744 | 8/1997 | |
| 2005/0075659 A1 | 4/2005 | Realyvasquez et al. | WO | 97/31575 | 9/1997 | |
| 2005/0075667 A1 | 4/2005 | Schaller et al. | WO | 97/32526 | 9/1997 | |
| 2005/0080454 A1 | 4/2005 | Drews et al. | WO | 97/40754 | 11/1997 | |
| 2005/0101975 A1 | 5/2005 | Nguyen et al. | WO | 97/42881 | 11/1997 | |
| 2005/0107871 A1 | 5/2005 | Realyvasquez et al. | WO | 98/19636 | 5/1998 | |
| 2005/0131429 A1 | 6/2005 | Ho et al. | WO | 98/30153 | 7/1998 | |
| 2005/0267572 A1 | 12/2005 | Schoon et al. | WO | 98/42262 | 10/1998 | |
| 2006/0004389 A1 | 1/2006 | Nguyen et al. | WO | 98/48707 | 11/1998 | |
| 2006/0253143 A1 | 11/2006 | Edoga | WO | 98/52475 | 11/1998 | |
| 2006/0271081 A1 | 11/2006 | Realyvasquez | WO | 99/07294 | 2/1999 | |
| 2006/0293701 A1 | 12/2006 | Ainsworth et al. | WO | 99/12484 | 3/1999 | |
| 2007/0010835 A1 | 1/2007 | Breton et al. | WO | 99/15088 | 4/1999 | |
| 2007/0027461 A1 | 2/2007 | Gardiner et al. | WO | 99/37218 | 7/1999 | |
| 2007/0106313 A1 | 5/2007 | Golden et al. | WO | 99/62406 | 12/1999 | |
| 2007/0142848 A1 | 6/2007 | Ainsworth et al. | WO | 99/62408 | 12/1999 | |
| | | | WO | 99/62409 | 12/1999 | |
| | FOREIGN PATENT DOCUMENTS | | WO | 99/62415 | 12/1999 | |
| DE | 0377052 | 6/1923 | WO | 99/63910 | 12/1999 | |
| DE | 2703529 | 1/1977 | WO | 99/65409 | 12/1999 | |
| DE | 3203410 | 5/1981 | WO | 00/03759 | 1/2000 | |
| DE | 3227984 | 2/1984 | WO | 00/15144 | 3/2000 | |
| DE | 3504202 | 8/1985 | WO | 00/59380 | 10/2000 | |
| DE | 4133800 | 10/1991 | WO | 00/60995 | 10/2000 | |
| DE | 4402058 | 4/1995 | WO | 00/64381 | 11/2000 | |
| DE | 19547617 | 9/1997 | WO | 00/74603 | 12/2000 | |

| | | |
|---|---|---|
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Chitwood Jr., Mitral Valve Repair: Ischemic, Mastery of Cardiothoracic Surgery, Lippencott-Raven Publishers, 1998, Chapter 32, pp. 309-321.

Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.

Grondin, et al., Carpentier's Annulus and De Vega's Annuloplasty: The end of the tricuspid challenge, Nov. 1975, vol. 70, pp. 852-861.

Holper, et al., Surgery for Tricuspid Insufficiency: Long Term Follow-Up After De Vega Annuloplasty, Thorac Cardiovasc Surgeon, 41, 1993.

Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.

Rabago, et al., The New De Vega Technique in Tricuspid Annuloplasty: Results in 150 patients, J. Cardiovas Surg. 1980, 21 pp. 231-238.

Rivera, et al., Carpentier's Flexible Ring Versus De Vega's Annuloplasty, J Thorac Cardiovas Surg, Feb. 1985, 89 pp. 196-203.

Wei, et al., De Vega's Semicircular Annuloplasty for Tricuspid Valve Regurgitation, Ann Thorac Surg, 1993, 55: pp. 482-485.

Wylie, et al., Manual of Vascular Surgery, R. H. Egdahl ed. Spring-Verlag: New York, vol. II, 1986, Table of Contents only.

Wylie, et al., Manual of Vascular Surgery, Springer-Verlag New York, vol. I, 1980, Table of Contents only.

Yun, et al. Mitral Valve Replacement, Mastery of Cardiothoracic Surgery, Lippencott-Raven Publishers, 1998, Chapter 34, pp. 329-341.

Yun, et al. Mitral Valve Replacement, Mastery of Cardiothoracic Surgery, Lippencott-Raven Publishers, pp. 329-341.

International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report on Patentability PCT/US2004/023728.
US 6,503,260, 01/2003, Schaller et al. (withdrawn)

* cited by examiner

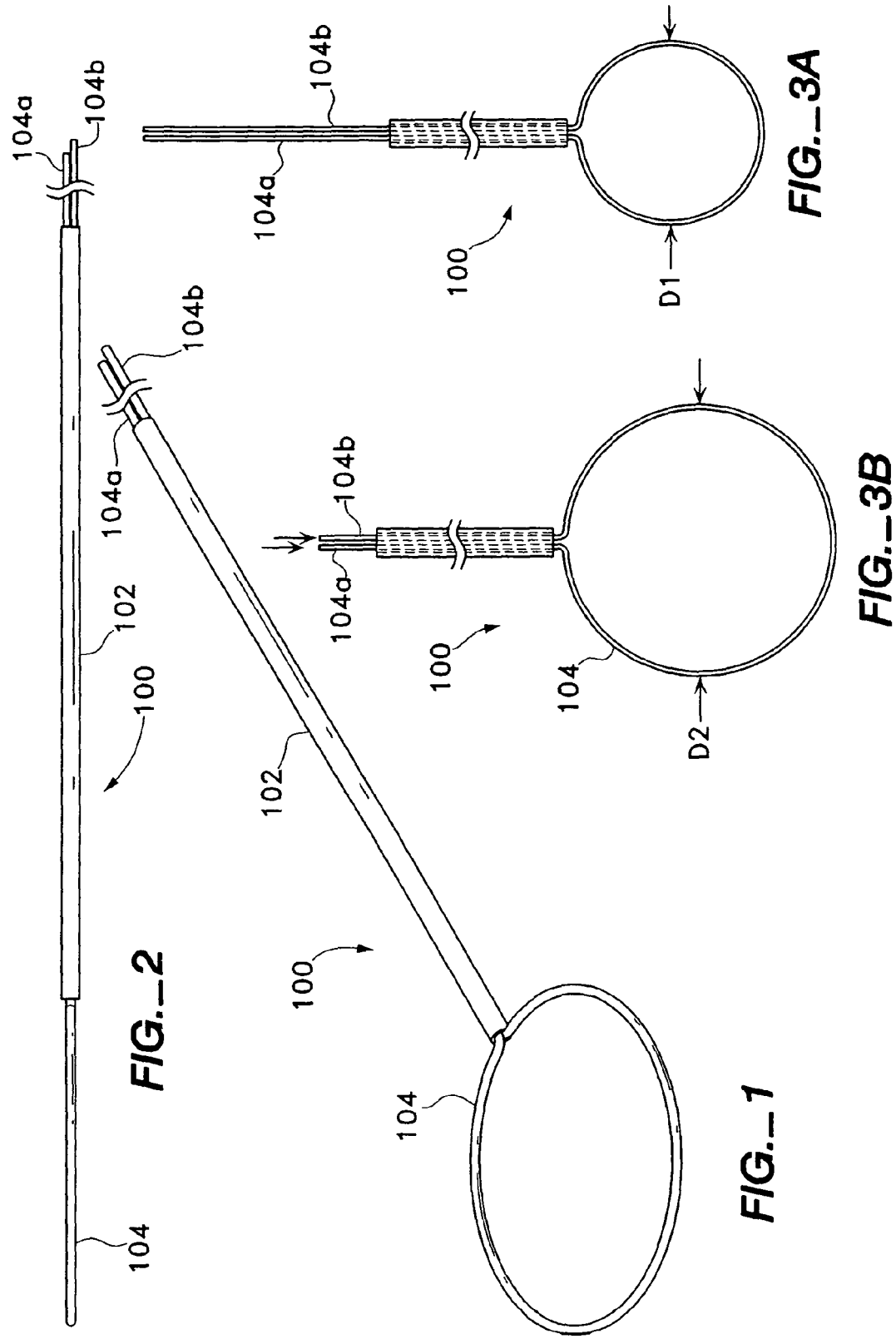

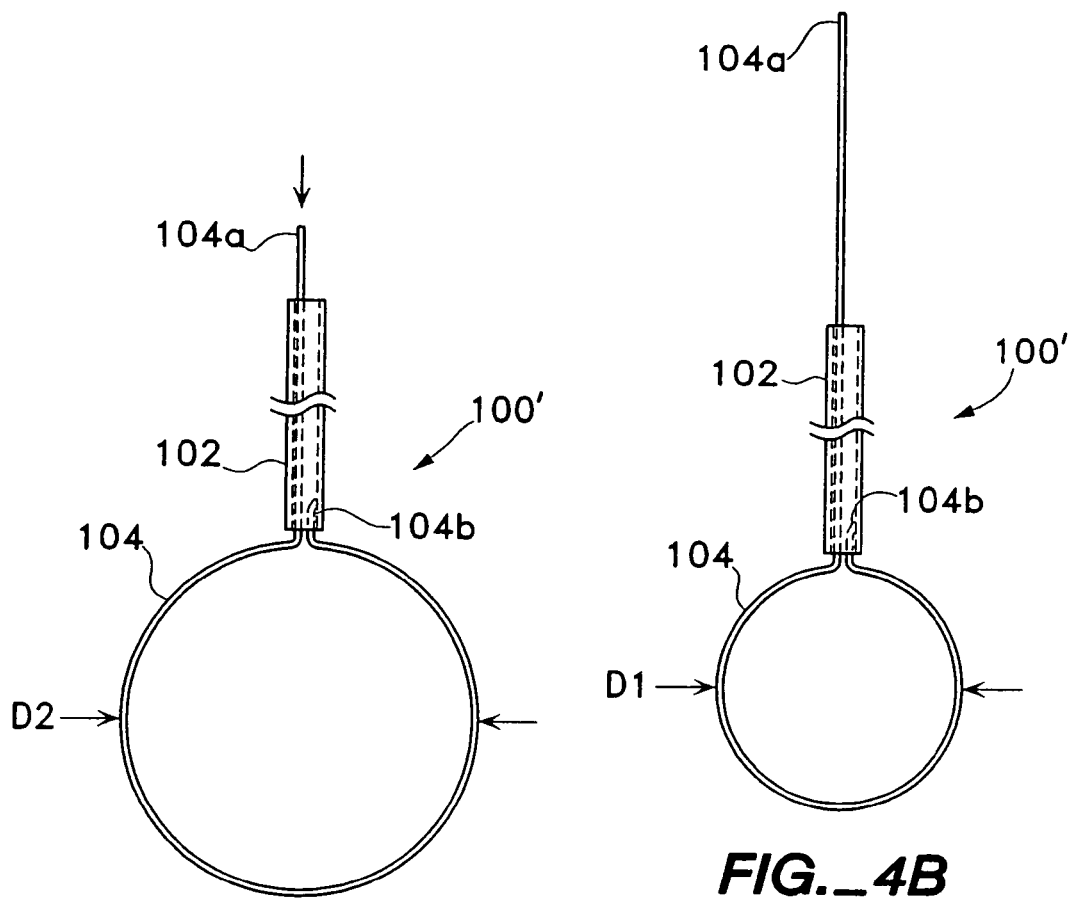
FIG._4A
FIG._4B
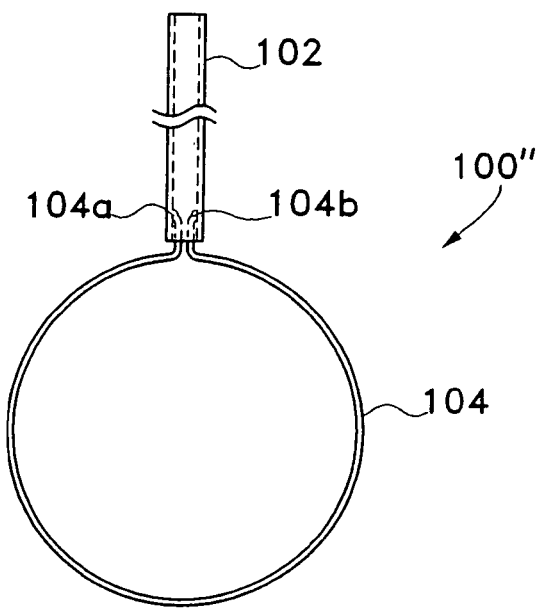
FIG._5

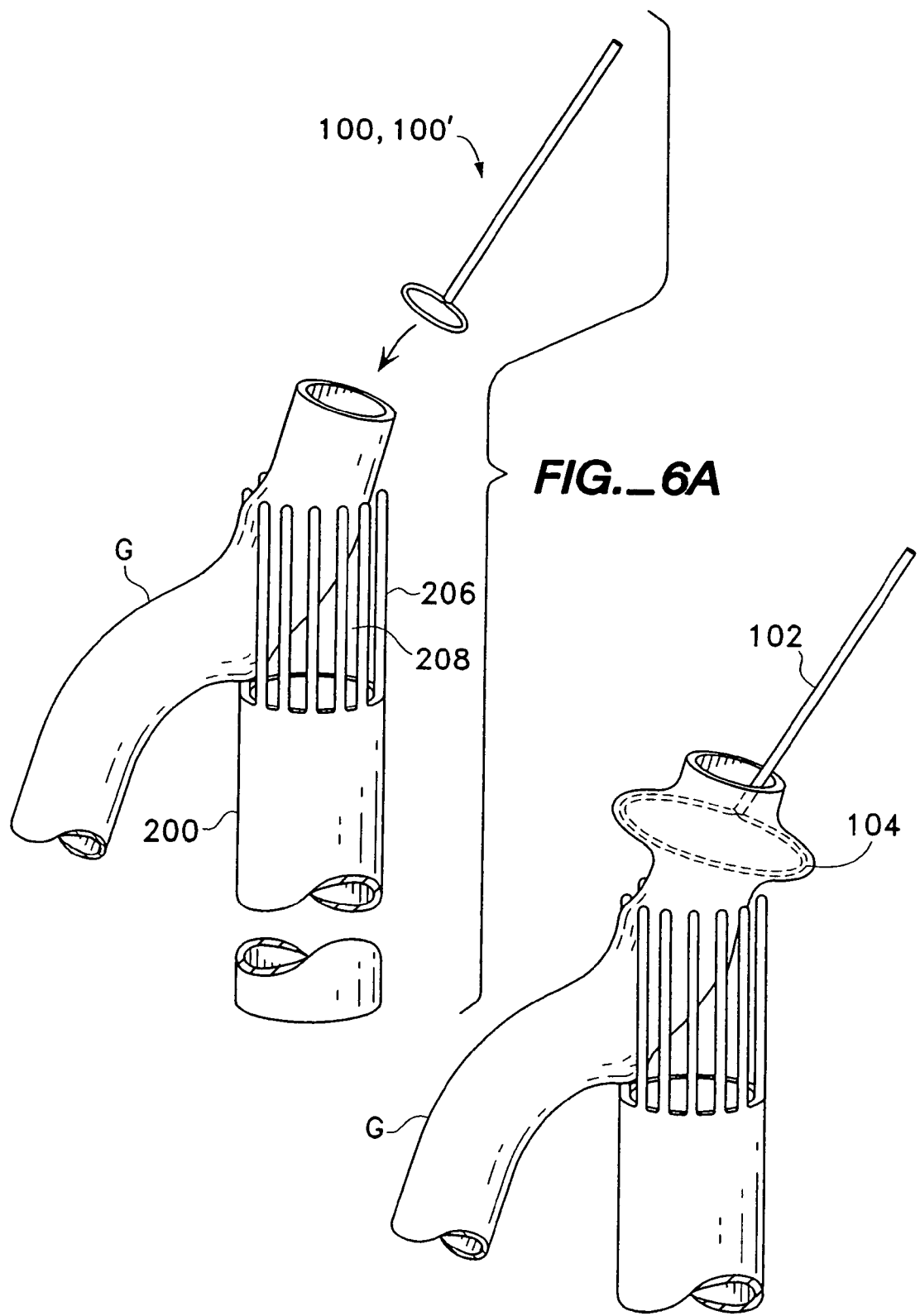
FIG._6A
FIG._6B

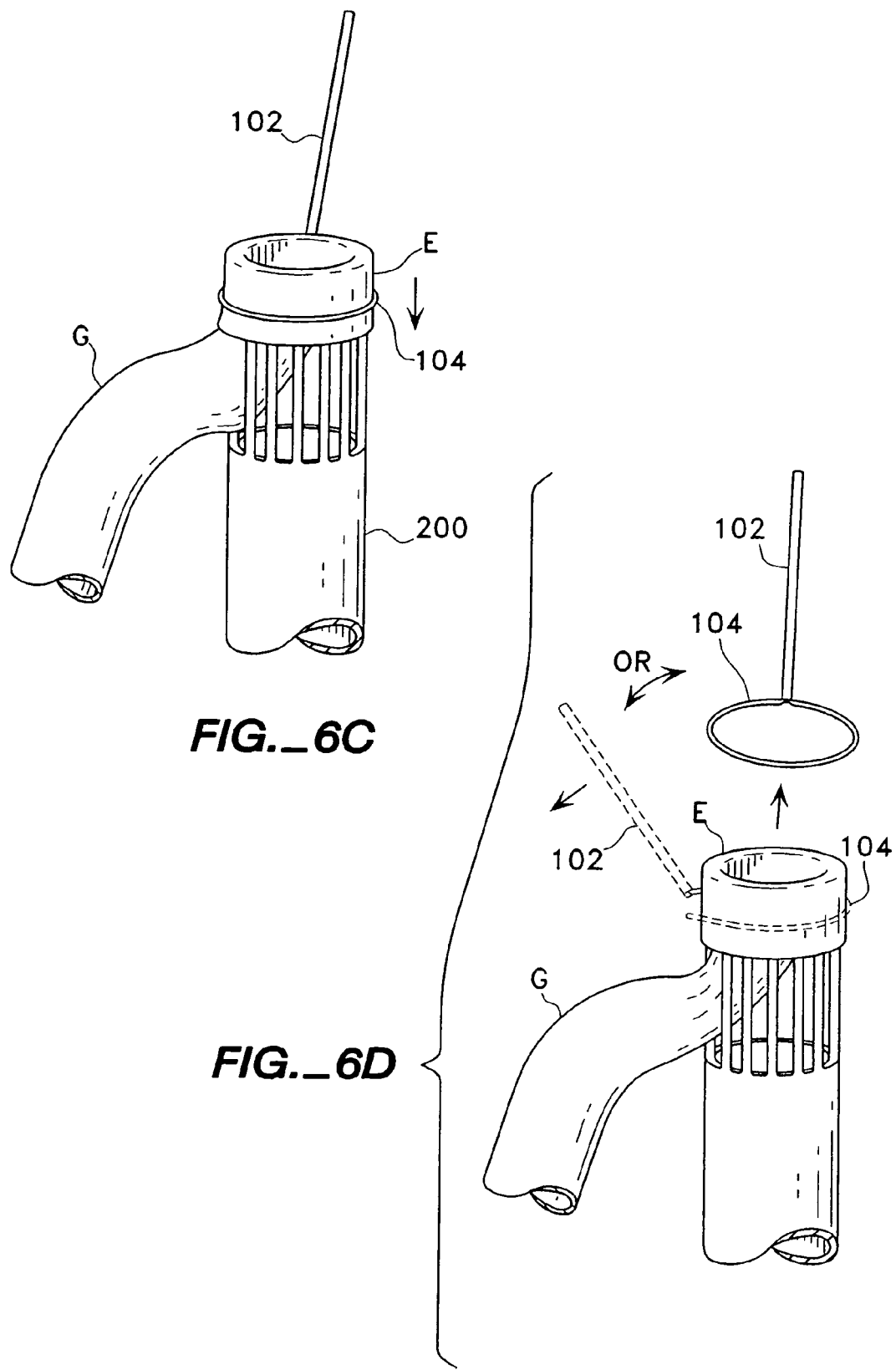
FIG._6C
FIG._6D

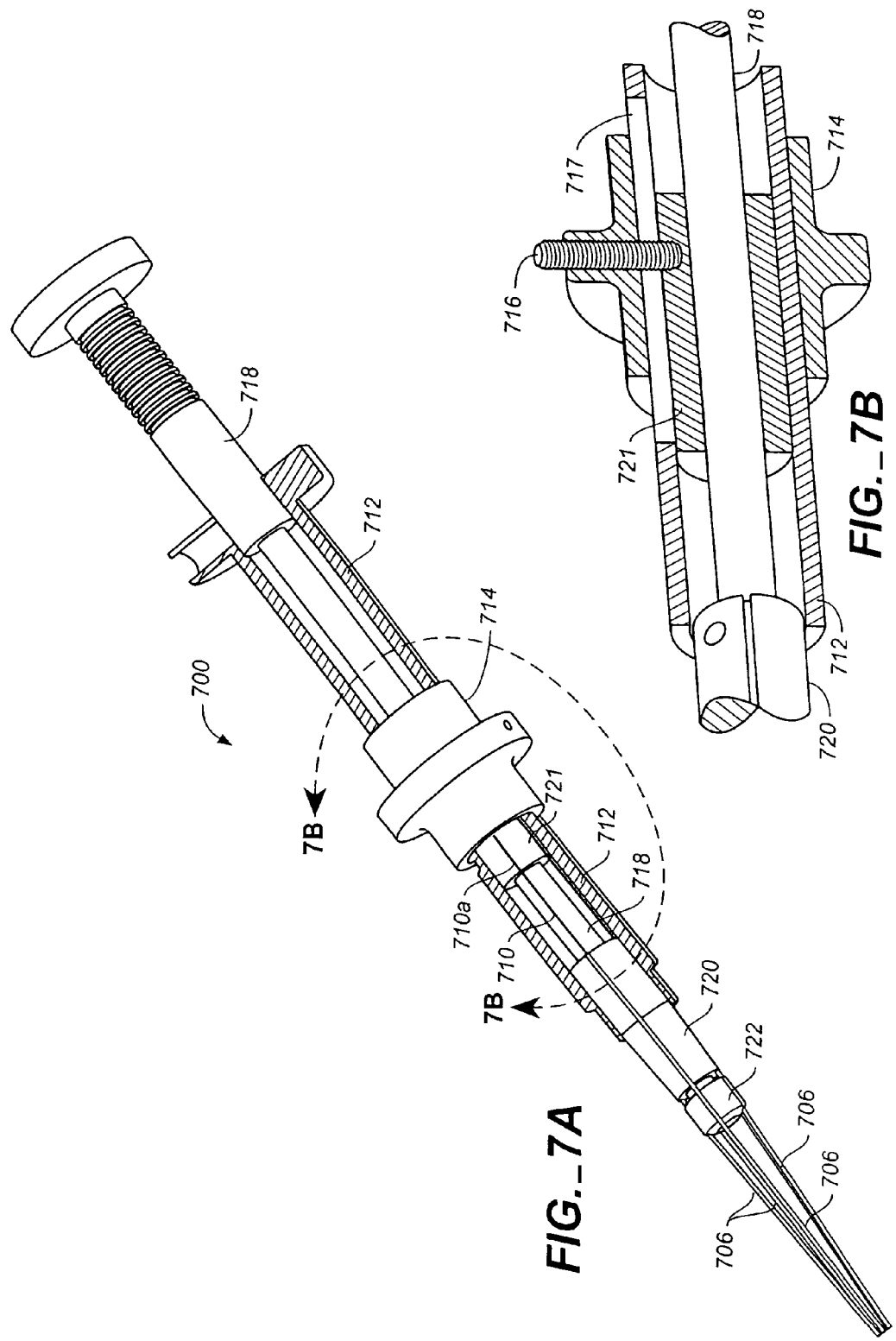

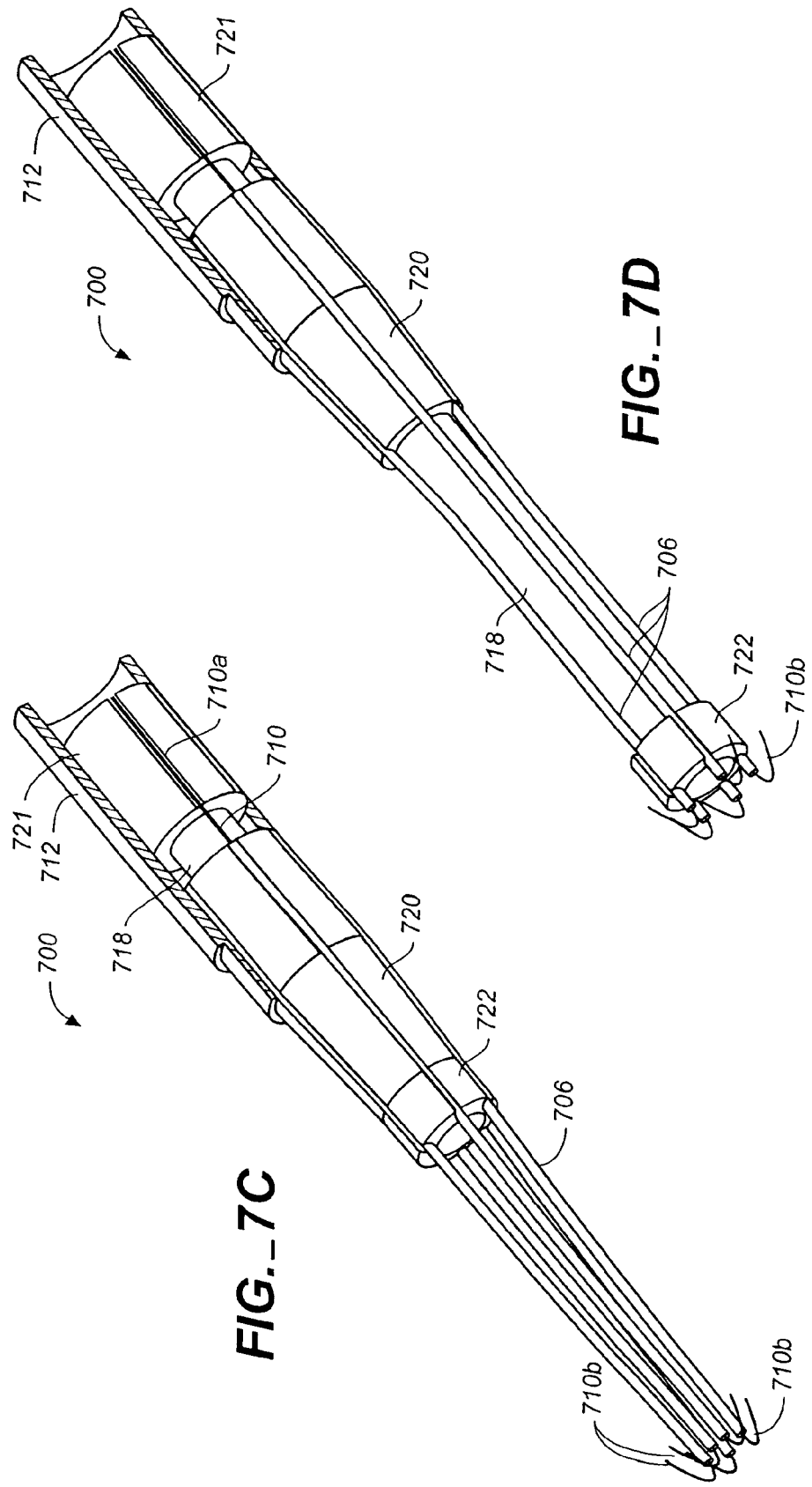

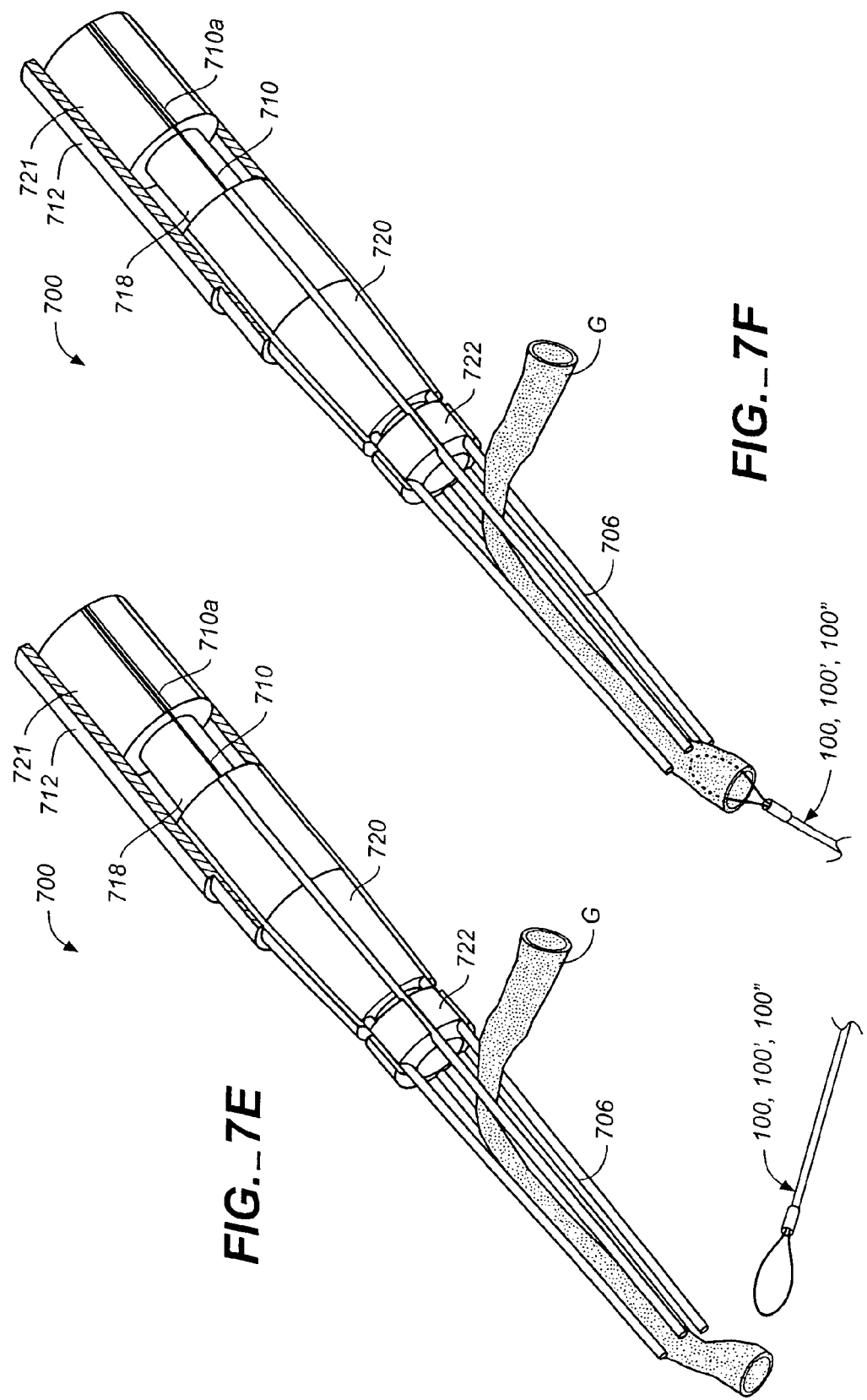

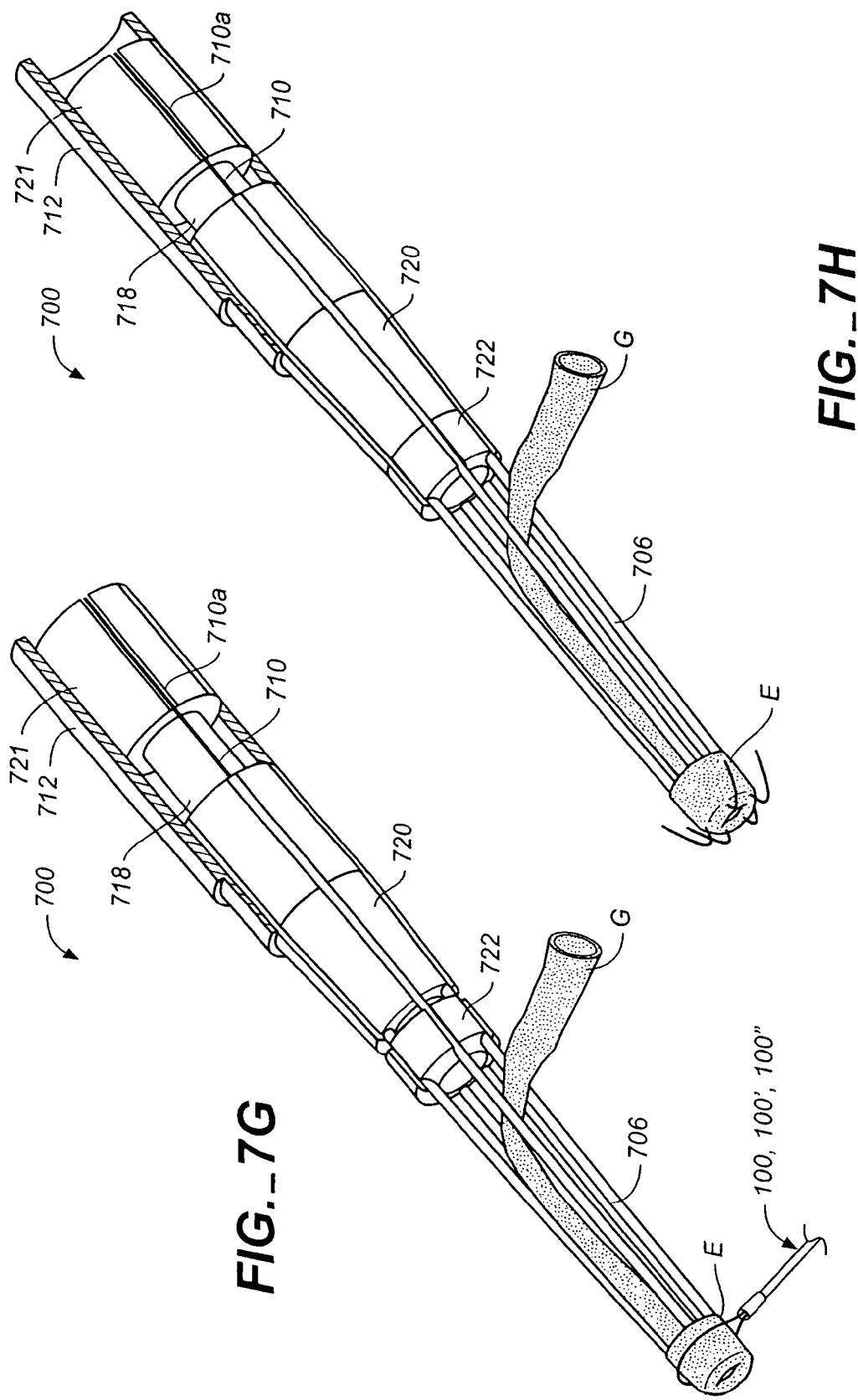

EVERSION APPARATUS AND METHODS

CROSS REFERENCE TO RELATED APPLICATION

This application is a divisional of U.S. patent application Ser. No. 10/646,254, filed Aug. 22, 2003, and now abandoned.

FIELD OF THE INVENTION

This invention relates to apparatus and methods for preparing a tubular graft for an anastomosis procedure. More particularly, the invention involves apparatus and methods for everting a graft prior to anastomosing the graft to another tubular structure such as an aorta.

BACKGROUND OF THE INVENTION

The occlusion of the arteries can lead to insufficient blood flow resulting in discomfort and risks of angina and ischemia. Significant blockage of blood flow in the coronary artery can result in damage to the myocardial tissue or death of the patient. In most cases, occlusion of the artery results from progressive long term deposits of plaque along the artery wall. While such deposits may be concentrated and occlude the artery at a particular site, the deposits are most certainly present throughout the arteries and the vascular system.

Coronary artery bypass graft (CABG) surgery is a surgical procedure performed in severe cases of coronary blockages. CABG procedures involve anastomosing an artery to a graft, such as a vascular graft, which restores the flow of blood by establishing another pathway around the occluded vasculature. During coronary artery bypass graft surgery, a vein or other conduit can be attached proximally to the patient's aorta. The other end is attached to the blocked artery, downstream from the obstruction, thus bypassing the coronary occlusion. CABG procedures can be done by placing the patient on a heart-lung machine and stopping the heart from beating or they can be done on a beating heart without a heart lung machine.

Vessel eversion apparatus have been disclosed to prepare vascular grafts for anastomosis. For example, vessel everting apparatus is described in U.S. Pat. No. 5,076,161 to Kirsch, et al. and U.S. Pat. No. 6,176,413 to Heck, et al. However, there remains a need to provide improved everting apparatus and methods.

SUMMARY OF THE INVENTION

The present invention involves improvements in anastomosis apparatus and methods for anastomosing a first tubular structure to a second tubular structure.

According to one embodiment of the invention, eversion apparatus for preparing a conduit, such as a vessel, for anastomosis in a human patient comprises an everting member having a loop shaped portion adapted to be inserted into an end portion of a conduit from a human patient and configured to fold a portion of the conduit end portion over itself when it is moved away from the conduit end and along the conduit while a portion of the conduit is held fixed relative thereto.

The eversion apparatus facilitates eversion of a vascular or nonvascular graft, for example, so that the intimal surface of the graft and the intimal surface of the target conduit, such as a vessel, can be placed in contact with one another for the anastomosis. The eversion apparatus also facilitates rapid graft eversion which can expedite the anastomosis procedure. In cases where the surgeon must complete the graft in as little time as possible due to the absence of blood flowing through a vessel such as the aorta in a CABG procedure, this can be especially advantageous. If blood flow is not promptly restored, sometimes in as little as 30 minutes, the tissues the artery supplies may experience significant damage or necrosis.

According to another embodiment of the invention, a conduit or vessel eversion system for preparing a conduit or vessel for anastomosis in a human patient comprises a conduit or vessel support device having a proximal end and a distal end; and everting apparatus comprising an everting member, the everting member having a loop shaped portion adapted to be inserted into a portion of a conduit or vessel to be prepared for an anastomosis in a human patient and evert the portion of the conduit or vessel over the conduit or vessel support device when the conduit or vessel is coupled to the support device with an end portion thereof extending from the distal end of the support device.

According to another embodiment of the invention, a method of everting a graft comprises positioning a graft in a support device such that an end portion of the graft extends therefrom; introducing a generally looped shaped member into the end portion of the graft extending from said support device; and moving the looped shaped member over the support device to fold at least a portion of the end portion of the graft over the support device The above is a brief description of some deficiencies in the prior art and advantages of the present invention. Other features, advantages, and embodiments of the invention will be apparent to those skilled in the art from the following description, accompanying drawings, wherein, for purposes of illustration only, specific forms of the invention are set forth in detail.

BRIEF DESCRIPTION OF THE DRAWINGS

FIG. 1 is a perspective view of an eversion tool constructed according to the principles of the present invention;

FIG. 2 is a side elevational view of the eversion tool of FIG. 1;

FIGS. 3A and 3B are top plan views of the eversion tool of FIG. 1 where FIG. 3A shows the everting member or loop adjusted to a first diameter and FIG. 3B shows the everting member or loop adjusted to a second larger diameter;

FIGS. 4A and 4B illustrate another embodiment of the eversion tool where FIG. 4A shows the everting member or loop adjusted to a first diameter and FIG. 4B shows the everting member or loop adjusted to a second larger diameter;

FIG. 5 illustrates another embodiment of the eversion tool;

FIGS. 6A-6D schematically illustrate everting a graft vessel using the eversion tool of any one of FIGS. 1-5, where FIG. 6A illustrates presenting the distal end portion of the graft vessel in a graft support device, FIG. 6B illustrates insertion of the eversion tool in the distal end portion of the graft vessel, FIG. 6C illustrates everting the distal end portion of the graft vessel, and FIG. 6D illustrates removing the eversion tool from the everted graft and graft support device;

FIGS. 7A-7D depicts another support or anastomosis device apparatus with which the eversion tool can be used, where FIG. 7A is a partial sectional view of the support device, FIG. 7B is an enlarged partial sectional view of the apparatus of FIG. 7A taken generally along line 7B-7B; FIG. 7C shows the apparatus of FIG. 7A in a radially collapsed state with the mandrel or slide retracted allowing the arms to progressively move radially inward along the distal portion thereof; and FIG. 7D shows the apparatus of FIG. 7A in a radially expanded state with the mandrel longitudinally extended toward the distal end of the apparatus urging the arms radially outward; and FIGS. 7E-7H illustrate everting a graft vessel using the eversion tool of any one of FIGS. 1-5, where FIG. 7E illustrates presenting the distal end portion of the graft vessel in the graft support device of FIG. 7A, FIG. 7F illustrates insertion of the eversion tool in the distal end portion of the graft vessel, FIG. 7G illustrates everting the distal end portion of the graft vessel with the eversion tool, and FIG. 7H illustrates extending piercing member through the distal end portion of the graft vessel after the eversion tool has been removed.

DETAILED DESCRIPTION OF THE INVENTION

Before the present invention is described, it is to be understood that this invention is not limited to the particular embodiments or examples described herein, as such may, of course, vary. Further, when referring to the drawings, like numerals indicate like elements.

The apparatus, systems, and methods described herein can be used to connect or anastomose tubular structures or conduits together. The tubular structures can be vascular or nonvascular structures. Thus, the apparatus, systems, and methods described herein can be used in connection with coronary artery bypass grafting procedures during which a vascular conduit or graft structure, such as a vein (e.g., a saphenous vein), artery (e.g., an internal mammary artery), or an artificial conduit or graft structure, is anastomosed to an aorta, the example target structure. They also can be used in connection with the anastomosis of internal mammary arteries to coronary arteries, and saphenous veins to coronary, femoral or popliteal arteries. The apparatus, systems, and methods described herein also can be used in connection with connecting other body lumens including nonvascular lumens, which can include, but are not intended to be limited to, the bile duct, the urethra, the urinary bladder, intestines, esophagus, stomach, and bowel.

The ideal anastomotic connection can be created when the component vessels are arranged in a situation that provides intima-to-intima contact. Standard suturing techniques provide some degree of this attribute, but there are inconsistencies owing to, for example, variation in operator technique and vessel preparation. To ensure providing exposure of the graft vessel intima, the vessel can be everted (or cuffed). This involves manipulation of the vessel to turn a defined section inside-out to expose the internal lumen and intimal surface. This everted section can also be utilized to create a seal (or gasket) between the graft and the native vessel. The everted section can be used to form the interface at the anastomotic site that also provides a medium for desired tissue healing. One difficulty of vessel eversion arises when attempting to manually manipulate the tissue to create the everted section or cuff. As the tissue is semi-elastic, it has a tendency to resist manual eversion.

The invention involves graft or vessel everting apparatus, systems and methods to prepare grafts and vessels for anastomosis and assist with the anastomosis. The eversion tool or apparatus of the present invention generally comprises an everting member, which comprises a flexible or pliable member or portion. The flexible or pliable member or portion can be semi-rigid and can be generally oval or circular with a closed or nearly closed turn. In other words, the flexible or pliable member or portion can be in the form of a loop. In operation, the everting member loop is inserted into one end of a graft or vessel and then manipulated to expand the graft or vessel radially outward so that the graft or vessel can be everted or draped over a vessel holder or support device, which will be described in more detail below. The everting member loop can have variable shapes and/or diameters to accommodate variously sized vessel support devices and to facilitate ease of its removal therefrom. The eversion tool also can include a handle to support the everting member.

Referring to FIGS. 1, 2, 3A, and 3B, one embodiment of an eversion tool constructed in accordance with the principles of the present invention is shown and generally designated with reference numeral 100. Eversion tool 100 generally comprises an everting member 104, which comprises a flexible or pliable member having a portion that is in the form of a circular loop. The generally circular loop can be nearly closed or closed. It should be understood, however, the flexible and/or pliable characteristics allow the loop to be readily reshaped. One suitable material for flexible or pliable member 104 can be stainless steel wire, such as 304 series stainless steel wire, or nitinol wire. The wire typically will have a diameter ranging from about 0.002 to 0.015 inch.

In the illustrative embodiment, eversion tool 100 includes handle 102 for supporting everting member 104. As shown in the illustrative embodiments, handle 102 can be tubular. It also can have a collar at its distal end as shown in FIGS. 7E-G. The handle can be made from any suitable material such as a machined metal (e.g., stainless steel) or injection molded plastic.

In the embodiment illustrated in FIGS. 3A and 3B, everting member 104 is slidably mounted in handle 102. More specifically, the ends of a straight wire (e.g., a nitinol wire) can be brought together and inserted into the handle without platically deforming the wire. This facilitates adjustment of the size of the everting member loop extending from handle 102 by moving the ends of the wire. One can move proximally located everting member ends 104a and 104b relative to handle 102 to adjust the length of the elongated everting member portion extending from the distal end of handle 102 to adjust the loop size. In FIG. 3A, the distal ends 104a and 104b are in first position and in FIG. 3B they have been moved in a distal direction as shown with arrows to enlarge the loop diameter from a first diameter D1 to a second larger diameter D2. From the position shown in FIG. 3B, either one or both of the distal ends can be moved proximally to return the loop diameter toward or to D1 or make the loop smaller than D1.

Referring to FIGS. 4A and 4B another embodiment of the eversion tool is shown and generally designated with reference numeral 100'. Eversion tool 100' is the same as eversion tool 100 with the exception that one portion of everting member 104 is fixedly secured to handle 102. In the example illustrated in FIGS. 4A and 4B, everting member 104b is fixedly secured to handle 102. Accordingly, one can enlarge the everting member loop diameter D1 as shown in FIG. 4A by moving or sliding everting member end 104a in a distal direction as shown with the arrow in FIG. 4B to enlarge diameter D1 to D2. One can retract everting member end 104a to return the loop diameter toward or to D1 or reduce the loop diameter to a diameter less than D1. According to further variations, the loop can be preformed with other shapes such as oblong, oval or teardrop shapes.

Referring to FIG. 5, another embodiment of the eversion tool is shown and generally designated with reference numeral 100". Eversion tool 100" is the same as eversion tool 100 with the exception that two portions of everting member 104 are fixedly secured to handle 102 so that the length of the loop extending from the distal end of the handle is fixed. In the illustrative embodiment, everting member ends 104a and 104b can be fixedly secured to handle 102.

Referring to FIGS. 6A-D, operation of the eversion tool will be described in conjunction with a graft support device which is schematically shown and generally indicated with reference numeral 200. In order to assist in the understanding of the operation of the eversion tool, graft support device 200 will first be described.

Anastomosis or support device 200 is used to hold the everted graft tubular structure (e.g., graft vessel) adjacent to or in an opening formed in a target tubular structure (e.g., target vessel) to which the graft tubular structure is to be anastomosed. More specifically, the support device supports or holds the graft tubular structure in a position relative to the target tubular structure so that the graft and target tubular structure can be secured to one another with known fasteners such as sutures or surgical clips.

Anastomosis or support device 200 comprises a proximal portion and a distal portion. The distal portion has a plurality of arms (or fingers) 206 that are configured to hold the everted portion or flap "E" of a tubular graft structure "G" as shown in FIGS. 6C and 6D. Adjacent arms are configured and arranged to form spaces, such as spaces 208, suitable for receiving surgical fasteners therethrough. Support device 200 can be described as a slotted tubular member, each slot having an open distal end and a closed end. After the support device has been positioned in the desired position and fasteners passed through a desired number of the slots through graft tubular structure and the target tubular structure, the open ends allow removal of the anastomosis or support device without disrupting the fasteners.

Anastomosis device or support 200 can be made from any suitable plastic or metal. For example, the device can be made from ABS plastic material or stainless steel tubing such as 304 stainless steel tubing. The length of the device typically ranges from about 25 mm to about 125 mm depending on the application. In aortic applications, it typically ranges from about 25 mm to about 70 mm. The inner diameter of the tube typically ranges from about 1 mm to about 25 mm also depending on the application. For example, the inner diameter typically can vary from about 3 mm to about 6 mm when sized for an aortic anastomosis where the tube thickness can range from 0.1 mm to 2 mm. On the other hand, the tube inner diameter can be up to about 25 mm when sized for applications concerning the bowel. The tube can have any number of slots or openings, but typically will have 4 to 12 slots cut into its side or the number of arms selected and arranged to form 4 to 12 openings. The slots or openings typically extend a length of about 2 mm to about 25 mm and have a width of about 0.2 mm to about 5 mm. In aortic applications, the slot length typically can range from about 5 mm to about 25 mm and the slot width typically can range from about 0.2 mm to 2.5 mm. The desired number of sutures or clips to be used for a particular anastomosis can determine the number of spaces or slots that the anastomosis device should have. That is the number of openings can match the number desired fasteners. However, it should be understood that the number of openings need not necessarily match the number of fasteners.

The tube can be split down the side to facilitate its placement in and removal from the tubular graft structure. Regarding the former, the split allows the tube to be compressed and deformed to fit into small openings in the target vessel. On the other hand, the split can be expanded to assist in removing the graft from the device. The tube can comprise or be made of shape memory material or alloy so that the compressed split tube returns to a shape memory tubular shape that is approximately equal to or slightly larger the opening into which it is inserted. The tube construction can provide for some elastic deformation in the radial direction if radially compressed so that its annular dimension can be decreased to some degree, which can be desirable when introducing the device into an opening formed in a vessel where the opening is slightly smaller in diameter than the diameter of device 200 in the uncompressed state. The wall thickness can be selected (e.g., reduced) to provide such elastic deformation. Other factors that can be used to achieve this effect include, but are not limited to a slot number, slit width, and material selection as would be apparent to one of skill in the art. For example, the tubular member can comprise or be made of nitinol.

Support device 200 can be cylindrical as shown in the drawings or it can have other shapes suitable for the intended purpose. For example, it can have a rectangular or oval configuration. Other construction examples include, but are not limited to, mesh tubes, wire framed constructions, or other nonsolid wall constructions.

Referring to FIG. 6A, tubular graft structure (e.g., graft vessel) "G" is passed between adjacent fingers 206 of support device 200 and the distal end thereof positioned to extend distally from the support device lumen. Alternatively, the tubular graft structure can be presented through the proximal end of support device 200 so that it passes along the length of the support device and extends from both the distal and proximal ends thereof. Eversion tool 100 or 100' is prepared for insertion into the distal end of the tubular graft structure. This can include bending the everting member portion that extends from handle 102 so that the plane in which the everting member loop lies forms an angle of about 90 degrees with the longitudinal axis of the handle as shown in FIG. 6A. The everting member loop is adjusted to have a diameter that allows it to be readily inserted into the end of graft G. The loop diameter can be selected to be less than the inner diameter of the end of graft G as shown in FIG. 6A. The everting member loop diameter is then enlarged to mechanically expand graft G, which in this example is semi-elastic, and increase the diameter of the graft as shown in FIG. 6B. The eversion tool is then moved so that the everting member passes over the distal end of the support device, thereby mechanically draping the expanded end of the graft over the support device distal end as shown in FIG. 6C. With the graft everted over support device 200, the eversion tool can be retracted as shown in FIG. 6D. Optionally, one can detach one end of everting member 104 from handle 102 for easier removal (FIG. 6D).

When eversion tool 100" is used with a fixed loop length, one typically does not bend the everting member to form an angle with handle 102. In this case, the loop is inserted into the graft and pulled over the graft support device as shown in FIGS. 7E-G, which will be described in detail below.

FIGS. 7A-D illustrate a support device 700 that also can be used in conjunction with eversion tool or apparatus 100, 100', or 100" in accordance with the principles of the present invention. Support device 700 is described in co-pending U.S. patent application Ser. Nos. 10/340,161 and 10/340,164, both of which were filed on Jan. 10, 2003 and entitled Anastomosis Apparatus and Methods.

Anastomosis or graft support device 700 generally includes a proximal portion and a distal portion, which includes a plurality of arms 706 in which piercing members 710 can be slidably mounted. More specifically, each arm forms a pathway in which a piercing member 710 is slidably mounted. Arms 706 can be tubular members (e.g., hypotubes) each having a lumen through which a piercing member 706 can slide.

Arms 706 are biased radially inward and have outer diameters that can range from 0.5 mm to 2 mm, for example, in aortic applications. In the illustrative embodiment, anastomosis apparatus 700 includes a mandrel or slide 722 for radially expanding the piercing member carrying or support arms 706.

Each arm 706 has a proximal end secured to tubular member or arm support 720 which tapers so that the annular dimension of the arms, taken collectively, progressively decreases in the distal direction when the slide 722 is in a retracted position adjacent to arm support 720 as shown in FIG. 7A. The arms can be secured in circumferentially spaced longitudinal grooves formed in arm support 720 by gluing or other suitable means. The arms also extend along longitudinal grooves formed in mandrel or slide 722. Actuator or plunger 718 extends through the device with its end secured to mandrel or slide 722 so that when the pusher is moved forwardly, it pushes the mandrel or slide 722 distally and radially expands the arms. After a graft is everted over the distal ends of the arms as will be described below, it can be desirable to radially expand the arms when graft holder or support 700 is positioned in an opening in a target tubular structure (e.g., target vessel) to which the tubular graft structure (e.g., graft vessel) is to be anatomosed. The radial expansion of the arms can enhance or form a seal between the graft and the target tubular structure (e.g., an aorta).

Referring to FIGS. 7C and 7D, apparatus or device 700 further includes piercing members 710, which are slidably mounted in arms 706. Piercing members 710 have proximal portions 710a and distal portions 710b. Piercing members 710 extend from arms 706 proximally toward cylindrical piercing member support 721 where proximal portions 710a are secured in grooves formed in cylindrical piercing member support 721. Support 721 is slidably mounted on actuator or pusher 718 and secured to cylindrical knob or finger grip 714 by fastener or screw 716 (FIG. 7B). When knob 714 is pushed forwardly in a distal direction, the piercing members are extended as shown in FIGS. 7C and 7D. Moving the knob 714 proximally retracts the piercing members as shown in FIG. 7A. Housing or tubular body 712 can have a longitudinal slot 717 through which screw 716 can slide so that knob 714 can move independently from housing 712.

The radius of curvature of the memory shaped distal portions 710b of the piercing members can vary. For example, a larger radius of curvature may be desired if the user wants to insert part of the device into the opening in the target structure or vessel to which the graft is to be anastomosed. On the other hand, a smaller radius of curvature may be desired if the user wants to tack the device down around the opening in the target structure or vessel, thereby seating the device on the outer wall and covering the opening with the graft.

Distal portions 710b have the desired memory shape to pierce the graft and vessel to which the graft is to be anastomosed when the piercing members are advanced. In the illustrative embodiment, the piercing members comprise shape memory material so that the distal portions 710b can be provided with a hook configured memory shape, which is one suitable shape for holding the graft and vessel together during the anastomosis. Thus, the piercing members can be made of nitinol wire and the distal portions provided with the desired memory shape as is known in the art so that they return to their memory shape when in an unbiased state (e.g., extended from arms 706). In other words, the shape memory alloy distal portions exhibit pseudoelastic (superelastic) behavior.

Referring to FIGS. 7E-G, eversion of a graft over the distal end portion of support member or apparatus 700 using any one of the eversion tools 100, 100', or 100" will be described. Graft structure (e.g., graft vessel) G is positioned in the graft support device or apparatus 700 with the distal end of graft structure G extending from the distal end of the support device as shown in FIG. 7E. The everting member loop of eversion tool 100 is introduced through the distal end of the graft structure and inserted into the graft lumen shown in FIG. 7F. The diameter of the everting member or loop can be increased as described above in connection with embodiments 100 and 100' to expand or increase the diameter of the graft vessel to make it easier to evert the distal end portion of the graft structure over the distal end of the graft holding device. The everting member loop is then turned or oriented so that it can pass over the distal end portion of the support member and moved to pass over the support member distal end portion or arms 706, thereby everting graft structure G over the support member distal end portion and forming everted portion E with the intimal surface of the graft lumen exposed and facing radially outward. In this manner the graft is prepared for an anastomosis where an intima-to-intima connection can be readily achieved. The support device can be positioned in an opening formed in the target tubular structure and the piercing members extended as shown in FIG. 7H to hold the graft and target tubular structures together, while fasteners are used to secure the graft and target structures together.

More specifically, after the surgeon cuts a hole or opening in the target tubular structure or vessel (e.g., the aorta) using a scalpel and an aorta cutting device or punch, the surgeon covers the hole with either a finger or other suitable tool. The distal portion of the support device and the portion of the graft everted thereover are positioned in the vessel opening. The distal portions of the piercing members are extended and the mandrel is moved distally to expand the arms and everted graft against the tissue surrounding the opening so as to form a seal therewith. In other words, the arms can be expanded to urge the everted graft against the tissue surrounding the target vessel opening to seal the connection between the graft and target vessel. After the fasteners have been placed to connect the graft and target tubular structures, the piercing members are retracted and anastomosis device 700 pulled off of the graft and target structures. Additional fasteners or clips can be placed at the connection, if any blood appears to be seeping out from the graft and target vessel.

Any fastener can be used to secure the tubular graft and target structures together. Examples of suitable fasteners include conventional sutures and surgical clips such as the surgical clips disclosed in U.S. Pat. No. 5,972,024 to Northrup, et al., U.S. Pat. No. 6,607,541 to Gardiner, et al., U.S. Pat. No. 6,514,265 to Ho, et al., U.S. Patent Publication No. 2002-0010490 of U.S. patent application Ser. No. 09/260,623 filed Mar. 1, 1999 and entitled Tissue Connector Methods and Apparatus and U.S. patent application Ser. No. 09/090,305 filed Jun. 3, 1998 and entitled Tissue Connector Apparatus and Methods.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. A method of everting a graft comprising:
   i) receiving a surgical eversion apparatus including a loop defined in a single plane the loop extending from a distal end of a handle wherein a longitudinal axis of the handle lies entirely in the single plane;
   ii) positioning a graft in a support device such that an end portion of the graft extends therefrom;
   iii) introducing the loop of the surgical eversion apparatus into the end portion of the graft extending from the support device, wherein the single plane has a first angular relationship relative to an axis of the end portion upon being introduced into the end portion;

iv) changing an orientation of the loop relative to the graft while the loop is within the end portion such that the single plane has a second angular relationship relative to the axis of the end portion, the second angular relationship being more perpendicular than the first angular relationship; and v) moving the loop over and around the support device such that the loop surrounds the support device to fold at least a portion of the end portion of the graft over the support device;

wherein a length of a perimeter of the loop is fixed throughout steps i-v.

2. The method of claim 1 wherein the graft comprises a tubular vascular graft.

3. The method of claim 1, wherein the first angular relationship is more parallel than the second angular relationship.

4. The method of claim 1, wherein changing an orientation of the loop includes pivoting the handle relative to the end portion.

5. The method of claim 1, wherein the loop is formed by a generally looped shaped member extending from the handle and terminating at opposing, first and second ends, the method further including:

detaching one of the first and second ends from the handle following the step of moving the loop over and around the support device.

6. The method of claim 1, wherein the loop comprises a wire, the wire extending continuously from the distal end to form the loop immediately adjacent the distal end.

7. The method of claim 1, wherein the loop defines an oval shape.

* * * * *